United States Patent [19]

Jolivet et al.

[11] Patent Number: 5,389,516

[45] Date of Patent: Feb. 14, 1995

[54] CDNA PROBES AND ANTIBODIES FOR HUMAN METHENYLTETRAHYDROFOLATE SYNTHETASE

[75] Inventors: Jacques Jolivet, Montréal, Canada; Alain Dayan, Tours, France; Richard Bertrand, Outremont, Canada

[73] Assignee: Universite de Montreal, Montreal, Canada

[21] Appl. No.: 33,857

[22] Filed: Mar. 19, 1993

[51] Int. Cl.$^6$ .................. C12N 15/11; C12N 15/12; C12N 15/52; C12Q 1/68

[52] U.S. Cl. ........................... 435/6; 536/23.2; 536/24.31; 935/14; 935/78

[58] Field of Search ............... 435/6; 536/24.1, 24.3, 536/24.31, 23.2

[56] References Cited

PUBLICATIONS

Ullman, B. et al., Proc. Natl. Acad. Sci. USA, 75:980–983, 1978.
Grem J. L. et al., Cancer Treat. Rep., 71:1249–64, 1987.
Bertrand R. et al., Bioch. Biophys. Acta, 911:154–61, 1987.

(List continued on next page.)

*Primary Examiner*—Robert A. Wax
*Assistant Examiner*—William W. Moore
*Attorney, Agent, or Firm*—Jacobson, Price, Holman & Stern

[57] ABSTRACT

The present invention relates to a cDNA probe for the detection of the mRNA for human methenyltetrahydrofolate synthetase, which comprises the following nucleic acid sequence, Seq. Id. No. 1:

```
                        G  GCC AAC   −1
ATG GTG AAA CCC CAT CTC TAT CAG
    AAA TAC AAA AGA ATT TCC ATC   45
TTT CTG AGC ATG CAA GAT GAA ATT
    GAG ACA GAA GAG ATC ATC AAG   90
GAC ATT TTC CAA CGA GGC AAA ATC
    TGC TTC ATC CCT CGG TAC CGG  135
TTC CAG AGC AAT CAC ATG GAT ATG
    GTG AGA ATA GAA TCA CCA GAG  180
GAA ATT TCT TTA CTT CCC AAA ACA
    TCC TGG AAT ATC CCT CAG CCT  225
GGT GAG GGT GAT GTT CGG GAG GAG
    GCC TTG TCC ACA GGG GGA CTT  270
GAT CTC ATC TTC ATG CCA GGC CTT
    GGG TTT GAC AAA CAT GGC AAC  315
CGA CTG GGG AGG GGC AAG GGC TAC
    TAT GAT GCC TAT CTG AAG CGC  360
TGT TTG CAG CAT CAG GAA GTG AAG
    CCC TAC ACC CTG GCG TTG GCT  405
TTC AAA GAA CAG ATT TGC CTC CAG
    GTC CCA GTG AAT GAA AAC GAC  450
ATG AAG GTA GAT GAA GTC CTT T   472
``` or any functional analogs thereof wherein the hybridization of the probe and the mRNA for human methenyltetrahydrofolate synthetase is substantially preserved. The present invention also relates to a polyclonal antibody or an antigen-binding fragment thereof for the detection of the mRNA for human methenyltetrahydrofolate synthetase, wherein said antibody is raised against a protein segment aa$^{100-112}$ H-Phe-Asp-Lys-His-Gly-Asn-Arg-Leu-Gly-Arg-Gly-Lys-OH, Seq. Id. No. 2 of human methenyltetrahydrofolate synthetase.

3 Claims, 4 Drawing Sheets

PUBLICATIONS

Mullin R. J. et al., "Then expanding role of folates and fluoropyrimidines in Cancer Chemotherapy", Plenum, New York, pp. 25-38, 1988.
Stover P. et al., J. Biol. Chem., 265:14227-14233, 1990.
Stover P. et al. J. Biol. Chem., 266:1543-1550, 1991.
Bertrand R. et al., J. Biol. Chem., 264:8843-6, 1989.
Hewick R. M. et al., J. Biol. Chem., 256:7990-7997, 1981.
Frohman M. A. et al., Proc. Natl. Acad. Sci. USA, 85:8998, 1988.
Hsu L. M. et al., J. Bacteriology, 161:1162-1170, 1985.
Ham, D. W., et al., 1988, The Journal of Biological Chemistry, 263(13):15946-15950.
Thiypen, A. E., et al, 1990, The Journal of Biological Chemistry 265(14):7907-7913.
Mascisch, A., and Rozon, R., 1991, Somatic Cell and Molecular Genetics, 17(4):391-398.
Peri, K. G., and Mackenzie, R. E., 1991, FEBS Letters, 294(1-2):113-115.

FIG. 1

```
MIRQRRRALTPEQQQEMGQQAATRMMTYPPVVMAHTVAVFLSFDGELDTQ    50 E.Coli
M               VKPHLY    QKYKRISIFLSMQDEIETE         26 Human
-                 -         ---   - -

PLIEQLWRAGKRVYLPVLHPF SAGNLLFLNYHPQ  SELVMNRLKIHEP    97 E.Coli
EIIKDIFQRGKICFIPRYR   FQSNHMDMVRIESPEEISLLPKTSWNIPQPG 76 Human
 -      --    -   --             - -

KLDVR DVLPLSRLDVLITPLVA FDEYGQRLGMGGGFYDRTLQNW QHYH   145 E.Coli
EGDVREEALSTGGLD LIFMPGLGFDKHGNRLGRGKGYYDAYLKRCLQHQE   126 Human
 ---    -  --          -  --- --    --

YKTQPVGYAHDCQLVEKLPVEEWDIPLPAVVTP SKVWEW              184 E.Coli
VKPYTLALAFKEQICLQVPVNENDMKVDEVLYEDSSTA                164 Human
 -   -  - --     -   -
```

FIG. 3

```
                              GC GAC ACT TAT AAA ATA ACT TGC ATC TAG GCT GGG   -91
CGT GGC GGC TCA CGC TGT AAT CCC AGC ACT TTG GGA GGC CGA AGT                    -46
GGG TGG ATC ACT TGA GGC CAG GAG TTT GAG ACC AGC CTG GCC AAC                     -1
ATG GTG AAA CCC CAT CTC TAT CAG AAA TAC AAA AGA ATT CCC ATC                     45
 M   V   K   P   H   L   Y   Q   K   Y   K   R   I   S   I                     15
                                                  -----IV-----
TTT CTG AGC ATG CAA GAT GAA ATT GAG ACA GAA GAG ATC ATC AAG                     90
 F   L   S   M   Q   D   E   I   E   T   E   E   I   I   K                     30
         ----IV----
GAC ATT TTC CAA CGA GGC AAA ATC TGC TTC ATC CCT CGG TAC CGG                    135
 D   I   F   Q   R   G   K   I   C   F   I   P   R   Y   R                     45

TTC CAG AGC AAT CAC ATG GAT ATG GTG AGA ATA GAA TCA CCA GAG                    180
 F   Q   S   N   H   M   D   M   V   R   I   E   S   P   E                     60
                                                  ---IV----
GAA ATT TCT TTA CTT CCC AAA ACA TCC TGG AAT ATC CCT CAG CCT                    225
 E   I   S   L   L   P   K   T   S   W   N   I   P   Q   P                     75

GGT GAG GGT GAT GTT CGG GAG GAG GCC TTG TCC ACA GGG GGA CTT                    270
 G   E   G   D   V   R   E   E   A   L   S   T   G   G   L                     90

GAT CTC ATC TTC ATG CCA GGC CTT GGG TTT GAC AAA CAT GGC AAC                    315
 D   L   I   F   M   P   G   L   G   F   D   K   H   G   N                    105
                           -------------I----------
CGA CTG GGG AGG GGC AAG GGC TAC TAT GAT GCC TAT CTG AAG CGC                    360
 R   L   G   R   G   K   G   Y   Y   D   A   Y   L   K   R                    120
         ------III------
TGT TTG CAG CAT CAG GAA GTG AAG CCC TAC ACC CTG GCG TTG GCT                    405
 C   L   Q   H   Q   E   V   K   P   Y   T   L   A   L   A                    135

TTC AAA GAA CAG ATT TGC CTC CAG GTC CCA GTG AAT GAA AAC GAC                    450
 F   K   E   Q   I   C   L   Q   V   P   V   N   E   N   D                    150
                         ---------------II---------------
ATG AAG GTA GAT GAA GTC CTT TAC GAA GAC TCG TCA ACA GCT TAA                    495
 M   K   V   D   E   V   L   Y   E   D   S   S   T   A   Z                    164
         -----------IV----------
ATC TGG ATT ACT ACA GCC AAA TAA TCA GTG TTT TAT ATG AGA GTA                    540
AAG CAA AGT ATG TGT ATT TTT CCC TTG TCA AAA ATT AGT TGA AAT                    585
TGT TCA TTA ATG TGA ATA CAG ACT GCA TTT TAA AAT TGT AAT TAT                    630
GAA ATA CCT TAT ATA AAA CCA TCT TTA AAA ACC AAT AGA AGT GTG                    675
AAT AGT AGA ATA TTA ATT AAA ATG GAG GCT ATC AGC CTG TGA TTT                    720
TCA GCT TAA AAA AAA AAA AAA A                                                  742
```

CDNA PROBES AND ANTIBODIES FOR HUMAN METHENYLTETRAHYDROFOLATE SYNTHETASE

BACKGROUND OF THE INVENTION (a) Field of the Invention

The invention relates to cDNA probes and antibodies for the detection of human methenyltetrahydrofolate synthetase (MTHFS) in biological tissue samples to determine the appropriate chemotherapy for a given patient treated with the reduced folate Leucovorin TM.

(b) Description of Prior Art

Many plant and animal tissues contain folic acid (pteroylglutamic acid) as the polyglutamates of the reduced tetrahydro forms. These folates act as coenzymes for processes in which there is transfer of a one-carbon unit (eg, in purine and pyrimidine nucleotide biosynthesis), amino acid conversions (e.g., histidine to glutamic acid through forminoglutamic acid), and generation and use of formate.

Absorption of folic acid takes place in the small intestine. In the epithelial cells folic acid are reduced to dihydro- and tetrahydrofolates. They are bound to protein and transported as methyl tetrahydrofolate. Serum levels vary from 3 to 21 ng/mL and closely reflect dietary intake. Red blood cell (RBC) folate, normal 160 to 640 ng/ml whole blood (corrected to packed cell volume of 45%), is a better indicator of the folate status. The total body folate is about 70 mg, ⅓ of which is found in the liver. About 20% of ingested folate is excreted unabsorbed together with 60 to 90 μg/day of ingested folate not reabsorbed from bile. Reduced folates are present in all living tissues although decreased amounts of certain reduced folates in cancer cells are thought to be responsible for the inefficacy of the anti-cancer agent 5-fluorouracil (Ullman, B. et al., Proc. Natl. Acad. Sci. USA, 75:980–983, 1978). 5-formyltetrahydrofolate is thus administered clinically, as Leucovorin TM, in association with 5-fluorouracil to enhance its cytotoxic effects through amplification of intracellular reduced folate pools (Grem JL et al., Cancer Treat. Rep., 71:1249–64, 1987).

Methenyltetrahydrofolatesynthetase (MTHFS; 5-formyltetrahydrofolate cyclodehydrase, EC 6.3.3.2), a 27 KDa monomer, catalyses the unidirectional transformation of 5-formyltetrahydrofolate to 5-10-methenyltetrahydrofolate and requires ATP and divalent cations. MTHFS activity has been purified from sheep liver, *Lactobacillus casei*, rabbit and human liver (Bertrand R. et al., Bioch. Biophys. Acta, 911:154–61, 1987).

MTHFS is the obligatory initial metabolic step prior to 5-formyltetrahydrofolate's intracellular conversion to other reduced folates and one experimental model suggests that variations in MTHFS activity between different tissues can influence intracellular 5-formyltetrahydrofolate interconversion to other reduced folates and its ability to enhance 5-fluorouracil activity (Mullin R. J. et al., "Then expanding role of folates and fluoropyrimidines in Cancer Chemotherapy", Plenum, N.Y., pp. 25–38, 1988). The enzyme might thus play a role in the cellular pharmacology of Leucovorin TM.

Physiologically, 5-formyltetrahydrofolate is produced through hydrolysis of 5-10-methenyltetrahydrofolate by a serine hydroxymethyltransferase-glycine complex (Stover P. et al., J. Biol. Chem., 265:14227–14233, 1990). The 5-formyltetrahydrofolate polyglutamates thus formed can then directly inhibit serine hydroxymethyltransferase, the main source of one carbon residues for folate-dependent syntheses (Stover P. et al. J. Biol. Chem., 266:1543–1550, 1991).

Inhibitory studies have demonstrated that MTHFS prevents 5-formyltetrahydrofolate polyglutamates from accumulating intracellularly and inhibiting de novo purine synthesis (Bertrand R. et al., J. Biol. Chem., 264:8843–6, 1989). MTHFS might thus also play an important physiological function in eliminating inhibitory 5-formyltetrahydrofolate polyglutamates.

A cDNA for human methenyltetrahydrofolate synthetase (MTHFS) has been isolated from a human liver cDNA library and sequenced. The nucleotide and derived amino acid sequences are unique and share a 28% amino acid homology with an *E. Coli* protein of unknown function. The identity of the cDNA was confirmed by immunizing rabbits with a 12 amino acid peptide chosen from the derived amino acid sequence and obtaining antibodies immunoblotting against human MTHFS.

There is a test, called "CEA test", for the determination of carcinoembryonic antigen (CEA) in the serum of a patient. CEA is present in the serum of 70% of patients with colo-rectal adenocarcinoma. However, the "CEA test" does not allow for the prognosis of a treatment of a patient with an anti-tumor agent.

It would be highly desirable to be provided with a test which would allow to predict the efficacy of Leucovorin TM-containing chemotherapy regimens in patients with colo-rectal malignancies.

SUMMARY OF THE INVENTION

One aim of the present invention is to provide for a prognostic test which would allow for the choice of an appropriate chemotherapy treatment for a given patient with colo-rectal carcinoma.

Another aim of the present invention is to provide for cDNA and antibodies to assay MTHFS in human colo-rectal tumors. A low enzyme expression would predict poor efficacy for Leucovorin TM-containing regimens and alert physicians not to administer potentially inefficient therapy.

Surprisingly and in accordance with the present invention there is provided a cDNA probe for the detection of human methenyltetrahydrofolate synthetase mRNA which comprises the following nucleic acid sequence (Seg. Id. No. 1):

|     |     |     |     |     |     |     |     |     |     |     |     |     |     | G   | GCC | AAC | −1  |
|-----|-----|-----|-----|-----|-----|-----|-----|-----|-----|-----|-----|-----|-----|-----|-----|-----|-----|
| ATG | GTG | AAA | CCC | CAT | CTC | TAT | CAG | AAA | TAC | AAA | AGA | ATT | TCC | ATC | 45  |
| TTT | CTG | AGC | ATG | CAA | GAT | GAA | ATT | GAG | ACA | GAA | GAG | ATC | ATC | AAG | 90  |
| GAC | ATT | TTC | CAA | CGA | GGC | AAA | ATC | TGC | TTC | ATC | CCT | CGG | TAC | CGG | 135 |
| TTC | CAG | AGC | AAT | CAC | ATG | GAT | ATG | GTG | AGA | ATA | GAA | TCA | CCA | GAG | 180 |
| GAA | ATT | TCT | TTA | CTT | CCC | AAA | ACA | TCC | TGG | AAT | ATC | CCT | CAG | CCT | 225 |
| GGT | GAG | GGT | GAT | GTT | CGG | GAG | GAG | GCC | TTG | TCC | ACA | GGG | GGA | CTT | 270 |
| GAT | CTC | ATC | TTC | ATG | CCA | GGC | CTT | GGG | TTT | GAC | AAA | CAT | GGC | AAC | 315 |
| CGA | CTG | GGG | AGG | GGC | AAG | GGC | TAC | TAT | GAT | GCC | TAT | CTG | AAG | CGC | 360 |
| TGT | TTG | CAG | CAT | CAG | GAA | GTG | AAG | CCC | TAC | ACC | CTG | GCG | TTG | GCT | 405 |
| TTC | AAA | GAA | CAG | ATT | TGC | CTC | CAG | GTC | CCA | GTG | AAT | GAA | AAC | GAC | 450 |

ATG AAG GTA GAT GAA GTC CTT T or any functional analogs thereof wherein the hybridization of the probe and the mRNA for human methenyltetrahydrofolate synthetase is substantially preserved.

Surprisingly and in accordance with the present invention, there is also provided an anti-MTHFS antibody or antigen-binding fragment thereof raised against a protein segment aa$^{100\text{-}112}$ (H-Phe-Asp-Lys-His-Gly-Asn-Arg-Leu-Gly-Arg-Gly-Lys-OH or H-FDKHGNRLGRGK-OH, Seq. Id. No. 2 of methenyltetrahydrofolate synthetase human MTHFS to assay MTHFS in a biological tissue sample.

There is also provided in accordance with the present invention, a Western blot method for determining the amount of MTHFS in a biological tissue sample, which comprises subjecting the biological tissue sample to an electrophoresis; incubating the electrophoresed biological sample with an anti-MTHFS antibody or antigen-binding fragment thereof specific to MTHFS, whereby the amount of MTHFS present in a biological tissue sample is determined by a Western blot analysis.

BRIEF DESCRIPTION OF THE DRAWINGS

FIG. 2 is the nucleotide and derived amino acid sequences of human methenyltetrahydrofolate synthetase cDNA, Seq. Id. No. 9;

DETAILED DESCRIPTION OF THE INVENTION

Protein purification and amino acid sequencing

Human liver MTHFS was purified to homogeneity as previously described by Bertrand R. et al. (Bioch. Biophys. Acta, 911:154–61, 1987). Purified enzyme was chemically cleaved with cyanogen bromide (CnBr) for 22 hours in 70% formic acid under an argon atmosphere and enzymatically digested by protease V8 for 15 hours in 20 mM Tris-HCl (pH 7.5). Following SDS-polyacrylamide electrophoresis in 18% vertical slab gels, fragments were transferred on polyvinylidene difluoride(PVDF) membrane prior to sequencing by automated Edman degradation performed on a model 470A TM Gas-phase sequencer equipped with an on-line model 120A TM phenylthiohydantoin analyzer (Applied Biosystem Inc.) employing the general protocol of Hewick et al. (Hewick R. M. et al., J. Biol. Chem., 256:7990–7997, 1981).

Molecular cloning

The first strand cDNA for polymerase chain reaction (PCR) was sythesized from human liver poly(A)+-RNA using Moloney TM murine leukemia virus reverse transcriptase (Stratagene, LaJolla Calif.). The 50 ul reaction contained 1 ug of poly(A)+RNA, 10 pmol of hybrid oligo dT$_{17}$-adapter primer (5'-CCCTCGAGGTCGACGGTATCGT$_{17}$-3' Seq. Id. No. 3), 25 units of enzyme and 250 uM of each dNTPs. Following incubation at 37° C. for 1 hour, an aliquot of the reaction mixture was amplified in 100 ul containing 50 mM KCl, 10 mM Tris-HCl (pH 8.3), 1.5 mM MgCl$_2$, 200 uM dNTPs, 10 units of Taq I TM DNA polymerase (Bethesda Research Laboratories), 10 pmoles of the adapter primer and 300 pmoles of degenerated oligonucleotides corresponding to a sequenced heptapeptide obtained from a CnBr fragment. The PCR product of 389 bp was then subcloned into Bluescript TM SK+ vector (Stratagene) for sequence analysis and was found to contain nucleotides corresponding to the primer sequence and to an open reading frame of 97 amino acids. This clone was then used as a probe to screen a λDR2 human liver cDNA library (Clontech, Palo Alto Calif.) at high stringency. Three hundred thousand plaques were screened and three positive clones were detected, plaque-purified, subcloned into pGEM and sequenced (Sequenase System, U.S. Biochemical Corp.).

Protein sequencing and cDNA cloning

Figure 1:
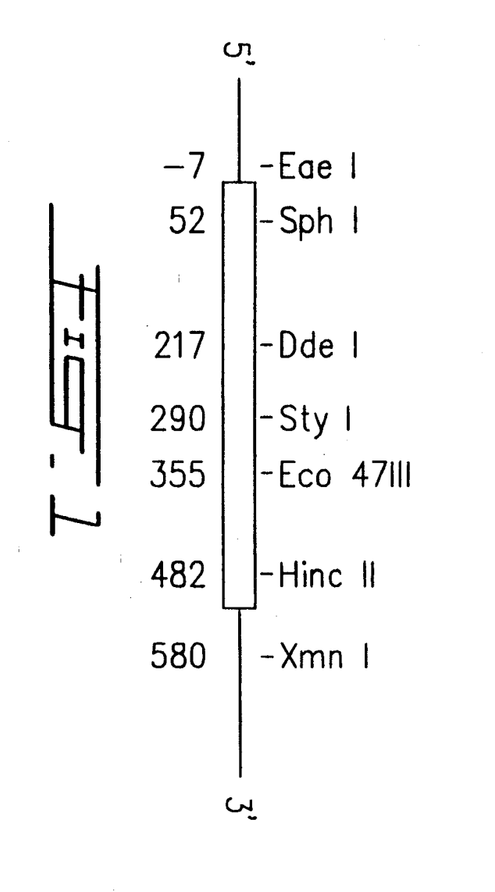
FIG. 1 is a partial restriction map of human methenyltetrahydrofolate synthetase cDNA.

A sequence of only six amino acids, Pro-Gly-Leu-Gly-Phe-Asp or PGLGFD, Seq. Id No. 4 , could be firmly established from one of the CnBr fragments due to the small amounts of the purified protein left after purification and was used for MTHFS cDNA cloning. A stretch of 10 amino acids, Gln-Ile-Cys-Leu-Gln-Val-Pro-Val-Asn-Glu or QICLQVPVNE, Seq. Id. No. 5 previously sequenced from a protease V8 digest had not been used to clone the MTHFS cDNA because the sequencing signals, while clearly readable, were judged to be too low to be certain of their accuracy. Degenerate oligonucleotides corresponding to an heptapeptide (Met was assumed to precede the sequenced hexapeptide) were used to amplify a 389 bp cDNA using a 3-' Arg-Ala-Cys-Glu (RACE), Seq. Id. No. 6 PCR protocol (Frohman M. A. et al., Proc. Natl. Acad. Sci. USA, 85:8998, 1988). This PCR product was subcloned for sequencing analysis and found to contain nucleotides corresponding to the primer sequence and to an open reading frame of 97 amino acids. This PCR product was then used as a probe to screen the λDR2 human liver cDNA library (Clontech) and a clone of 867 bp was a Met initiation translation codon preceded by a kozac consensus motif (FIG. 1). The 5-' and 3-' untranslated regions are 125 and 247 bp respectively. The open reading frame corresponds to a sequence of 164 amino acids. The resulting protein contains the two sequenced peptides obtained from purified MTHFS protein (I and II, FIG. 1), an ATP consensus binding site (III, FIG. I) and 4 consensus putative phosphorylation sites (IV, FIG. 1).

The human liver MTHFS nucleic acid sequence with the coding region indicated by its amino acid sequence underneath as illustrated in FIG. 2.

Figure 3:
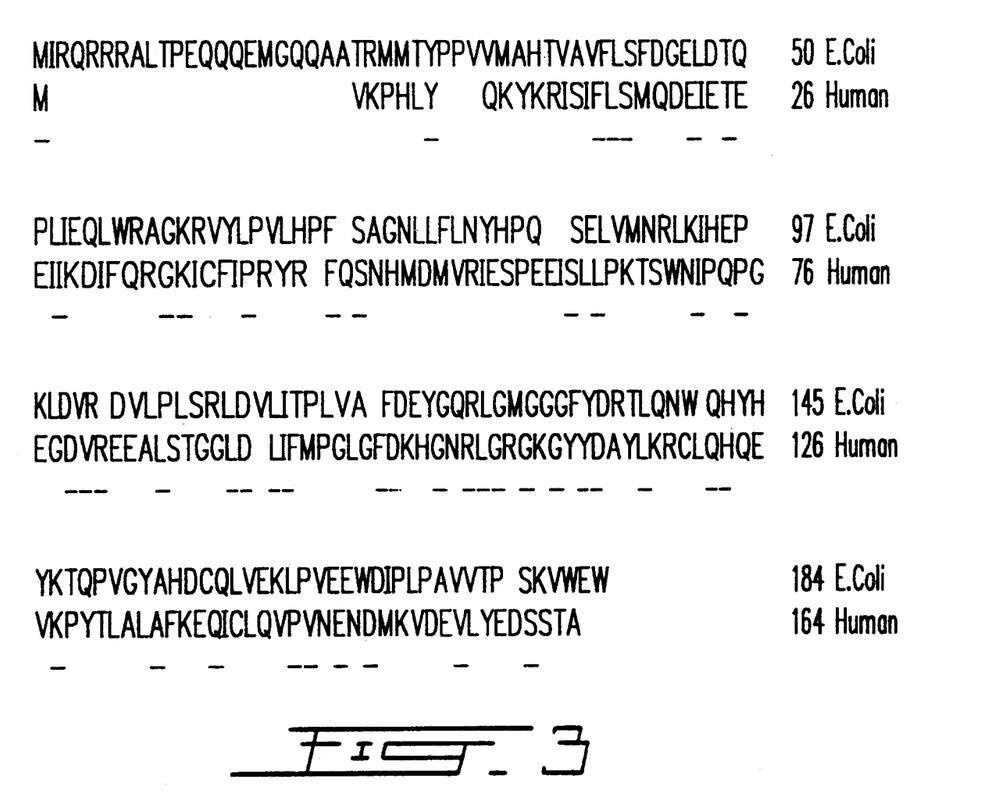
FIG. 3 is an alignment of the amino acid sequence of human methenyltetrahydrofolate synthetase cDNA, Seq. Id. No. 8 with those of an E.coli protein of unknown function, Seq. Id. No. 7.

The sequence from the 867 bp clone was used to search the Gen Bank TM /EMBL Data Bank. This revealed a 28% amino acid homology with a bacterial protein of unknown function (FIG. 3) (Hsu L. M. et al., J. Bacteriology, 161:1162–1170, 1985). The sequence of this E. coli protein was deduced from a 540 nucleotide sequence open reading frame (ORF) placed immediately after a 6S RNA gene and encodes for a 21 kD protein. There is also a 92% homology between nucleotides 30 to 160 in the 5' non-coding region and the first monomer of Alu type sequences.

In accordance with the present invention, both cDNA probes and antibodies for the detection of MTHFS may be used to determine the level in a given biological sample of MTHFS which is associated with human tumors. Low enzyme expression would predict poor efficacy for Leucovorin TM-containing regimens and alert physicians not to administer potentially inefficient therapy.

Biological tissue samples in accordance with the present invention may be neoplastic tissues, such as human colo-rectal tumor extracts or extracts from any other malignant tissues, and corresponding normal tissues of a given patient.

The level of the MTHFS enzyme in a biological sample may be measured in Mol/mg tissue.

A low level of the MTHFS enzyme in a given neoplastic tissue sample may be determined by comparison to the level of MTHFS in the normal tissue of the patient.

EXAMPLE I cDNA probe useful for the detection of Human MTHFS mRNA cDNA probes for the detection of the mRNA of human methenyltetrahydrofolate synthetase (MTHFS) are obtained by using a restriction fragment (EaeI/HincII) as a probe. The resulting probe has the following nucleic acid (-7-472 bp of MTHFS) sequence, Seq. Id. No. 1.

sized by a solid-phase technique, using a scheme based on t-Boc chemistry/acid labile amino acid protecting groups. The crude peptide was purified in one step by preparative high pressure liquid chromatography (HPLC) on a Partisil 10 ODS-3 Whatman TM column (10μ particle size; 2.2 cm×50 cm), using a binary solvent system consisting of 0.01% trifluoroacetic acid (TFA), pH 2.9 and acetonitrile (CH₃CN)-0.01% TFA and an appropriate gradient. Elution of the peptide was monitored at 214 nm. Collected fractions were screened by analytical HPLC using UV detection, pooled accordingly, evaporated in vacuo and lyophilized twice. The purified peptide was analyzed for homogeneity by analytical HPLC on a μBondapak C18 TM column (10μ particles; 0.39×15 cm) using appropriate linear gradients of 0.01% TFA, pH 2.9 and CH₃CN-0.01% TFA and 0.01M ammonium acetate, pH 6.9 and CH₃CN. Its amino acid composition was assessed by quantitative amino acid analysis after acidic hydrolysis in vacuo (6N HCl, 110° C., 118 hours) and phenylisothiocyanate derivatization. Peptide purity was 99% as assessed by reverse-phase HPLC. Amino acid composition (Asx (2), 1.88; G (3), 2.92; H (1), 1.03; R (2), 2.29; L (1), 0.94; F(1), 0.99; K (2), 1.94) and peptide content (70%) were satisfactory.

The pure peptide was adsorbed onto methylated bovine serum albumin (mBSA) as carrier protein, at a ration of 5 mg peptide/1 mg mBSA and rabbit immunization was performed.

The identity of the cDNA was confirmed by immunizing rabbits with a 12 amino acid peptide (Phe-Asp-Lys-His-Gly-Asn-Arg-Leu-Gly-Arg-Gly-Lys, Seq. Id. No. 1 or FDKHGNRLGRGK) chosen from the derived amino acid sequence aa$_{100\text{-}112}$ of MTHFS.

Antibodies were obtained after the third booster in-

|     |     |     |     |     |     |     |     |     |     |     |     | G   | GCC | AAC | −1  |
|-----|-----|-----|-----|-----|-----|-----|-----|-----|-----|-----|-----|-----|-----|-----|-----|
| ATG | GTG | AAA | CCC | CAT | CTC | TAT | CAG | AAA | TAC | AAA | AGA | ATT | TCC | ATC | 45  |
| TTT | CTG | AGC | ATG | CAA | GAT | GAA | ATT | GAG | ACA | GAA | GAG | ATC | ATC | AAG | 90  |
| GAC | ATT | TTC | CAA | CGA | GGC | AAA | ATC | TGC | TTC | ATC | CCT | CGG | TAC | CGG | 135 |
| TTC | CAG | AGC | AAT | CAC | ATG | GAT | ATG | GTG | AGA | ATA | GAA | TCA | CCA | GAG | 180 |
| GAA | ATT | TCT | TTA | CTT | CCC | AAA | ACA | TCC | TGG | AAT | ATC | CCT | CAG | CCT | 225 |
| GGT | GAG | GGT | GAT | GTT | CGG | GAG | GAG | GCC | TTG | TCC | ACA | GGG | GGA | CTT | 270 |
| GAT | CTC | ATC | TTC | ATG | CCA | GGC | CTT | GGG | TTT | GAC | AAA | CAT | GGC | AAC | 315 |
| CGA | CTG | GGG | AGG | GGC | AAG | GGC | TAC | TAT | GAT | GCC | TAT | CTG | AAG | CGC | 360 |
| TGT | TTG | CAG | CAT | CAG | GAA | GTG | AAG | CCC | TAC | ACC | CTG | GCG | TTG | GCT | 405 |
| TTC | AAA | GAA | CAG | ATT | TGC | CTC | CAG | GTC | CCA | GTG | AAT | GAA | AAC | GAC | 450 |
| ATG | AAG | GTA | GAT | GAA | GTC | CTT | T   |     |     |     |     |     |     |     | 472 |

Figure 4:
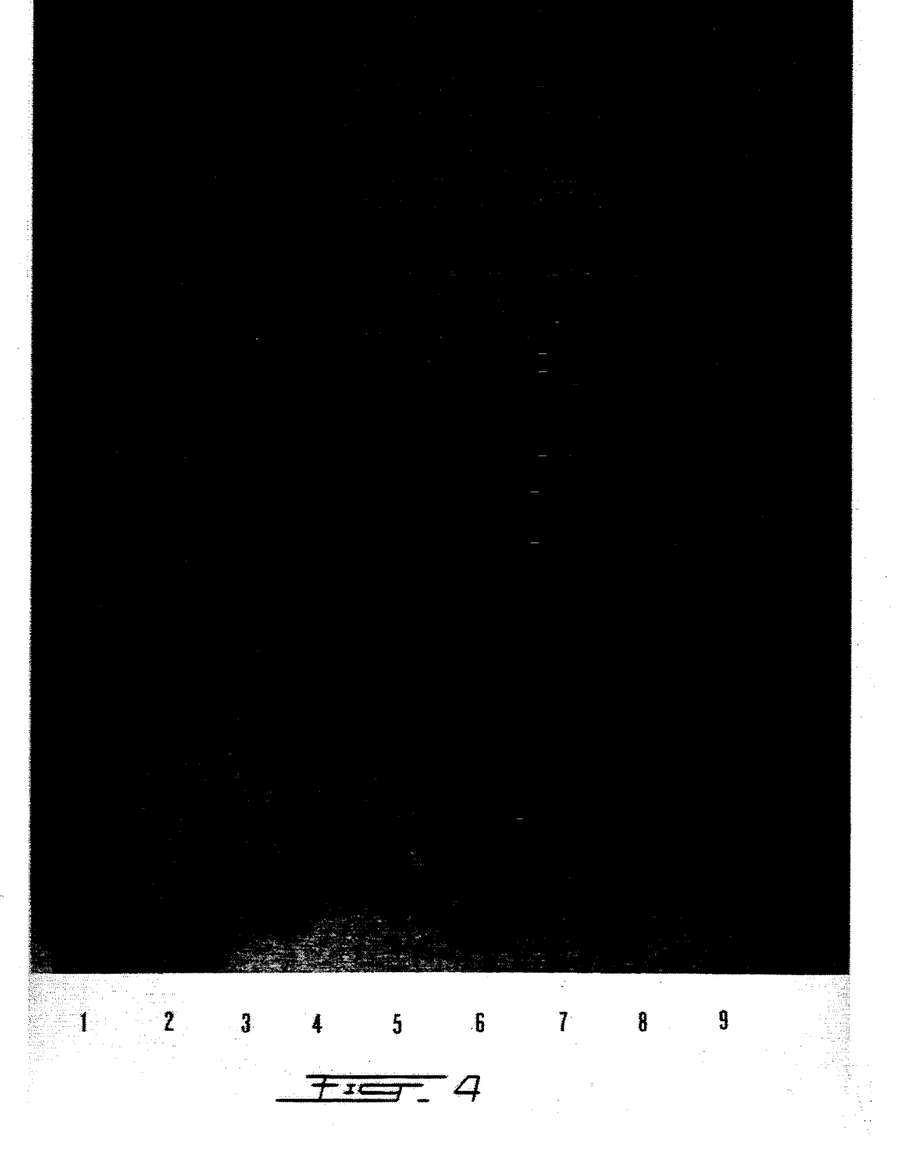
FIG. 4 is a Northern blot of polyA RNA from normal human tissue using $^{32}$P-labeled 238 bp restriction fragment (Sph I/Sty I) of human methenyltetrahydrofolate synthetase cDNA as a probe.

FIG. 4 shows a Northern blot of polyA RNA from normal human tissues. The hybridization was carried out with ³²P-labeled 238 bp restriction fragment (Sph I/Sty I) of human methenyltetrahydrofolate synthetase cDNA as a probe. The human tissues of FIG. 4 are as follows: 2) heart, 3) brain, 4) placenta, 5) lung, 6) liver, 7) skeletal muscle, 8) kidney, and 9) pancreas. The transcript is approximately 0.9 kb in size.

The above-described cDNA may be used to assay the level in a given biological sample of MTHFS which is associated with human tumors. Low enzyme expression would predict poor efficacy for Leucovorin TM-containing regimens and alert physicians not to admininister potentially inefficient therapy.

EXAMPLE II

Anti-MTHFS antibody

A peptide representing the protein segment 100–112 (H-Phe-Asp-Lys-His-Gly-Asn-Arg-Leu-Gly-Arg-Gly-Lys-OH or H-FDKHGNRLGRGK-OH, Seq. Id. No. 2) of methenyltetrahydrofolate synthetase was synthejection which reacted against both the immobilized peptide on nitrocellulose and purified human MTHFS on Western blot.

Western blot analysis

Figure 5A:
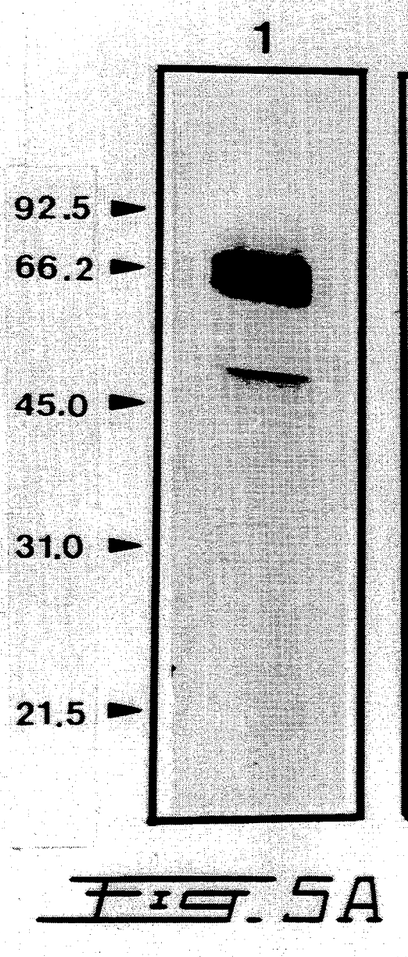
FIG. 5 is a Western blot of pre-immune rabbit serum and polyclonal immune rabbit serum raised against a dodecapeptide (aa$_{100\text{-}112}$) of human liver methenyltetrahydrofolate synthetase.
Figure 5B:
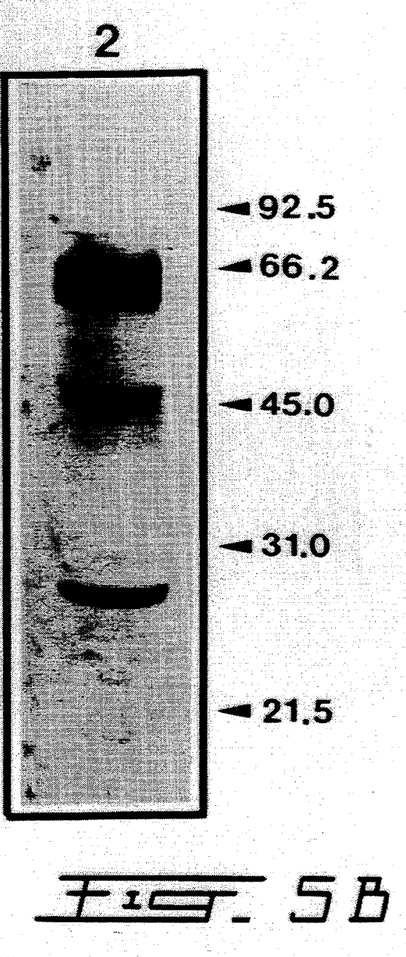

Partially purified MTHFS from human liver was electrophoresed on SDS-polyacrylamide gels (11%), transferred to nitrocellulose and incubated with the obtained rabbit serum after immunization. Human MTHFS proteins were detected with alkaline-phosphatase conjugated antibodies (BRL, Gaithersburg, Md.). The Western blot analysis is shown in FIG. 5 where the arrows and the numbers indicate the migration positions and the size of the Mr markers (kDA).

The antibodies of the present invention may be used to assay the level in a given biological sample of MTHFS which is associated with human tumors. Low enzyme expression would predict poor efficacy for Leucovorin TM-containing regimens and alert physicians not to administer potentially inefficient therapy.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A cDNA probe for the detection of the mRNA for human methenyltetrahydrofolate synthetase, which comprises at least one nucleic acid sequence, selected from the group consisting of:

```
                            G GCC AAC                                 -1

ATG GTG AAA CCC CAT CTC TAT CAG
    AAA TAC AAA AGA ATT TCC ATC                                       45

TTT CTG AGC ATG CAA GAT GAA ATT
    GAG ACA GAA GAG ATC ATC AAG                                       90

GAC ATT TTC CAA CGA GGC AAA ATC
    TGC TTC ATC CCT CGG TAC CGG                                       135

TTC CAG AGC AAT CAC ATG GAT ATG
    GTG AGA ATA GAA TCA CCA GAG                                       180

GAA ATT TCT TTA CTT CCC AAA ACA
    TCC TGG AAT ATC CCT CAG CCT                                       225

GGT GAG GGT GAT GTT CGG GAG GAG
    GCC TTG TCC ACA GGG GGA CTT                                       270

GAT CTC ATC TTC ATG CCA GGC CTT
    GGG TTT GAC AAA CAT GGC AAC                                       315

CGA CTG GGG AGG GGC AAG GGC TAC
    TAT GAT GCC TAT CTG AAG CGC                                       360

TGT TTG CAG CAT CAG GAA GTG AAG
    CCC TAC ACC CTG GCG TTG GCT                                       405

TTC AAA GAA CAG ATT TGC CTC CAG
    GTC CCA GTG AAT GAA AAC GAC                                       450

ATG AAG GTA GAT GAA GTC CTT T                                         472
```

Seq. Id. No. 1 and a 238bp SphI/StyI restriction endonuclease fragment thereof.

2. A Northern blot method for determining the amount of MTHFS transcript in a biological tissue sample, which comprises the steps of:
   a) labelling the cDNA probe of claim 1,
   b) isolating the mRNA present in a biological tissue sample and separating said mRNA on the basis of relative mass by gel electrophoresis; and,
   c) incubating the electrophoresed biological sample of step b) with the labelled cDNA probe of step a), whereby the amount of MTHFS transcript present in said biological sample is determined.

3. The method of claim 2, wherein the biological tissue sample is taken from a patient eligible for a 5-formyltetrahydrofolate-containing chemotherapy regimen, wherein the determination of the amount of MTHFS transcript present in the tissue sample allows determination of whether a 5-formyltetrahydrofolate-containing chemotherapy would be efficacious if applied.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 479 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: YES

( i v ) ANTI-SENSE: NO

( x i ) SEQUENCE DESCRIPTION: SEQ ID NO:1:

```
GGCCAACATG  GTGAAACCCC  ATCTCTATCA  GAAATACAAA  AGAATTTCCA  TCTTTCTGAG       60
CATGCAAGAT  GAAATTGAGA  CAGAAGAGAT  CATCAAGGAC  ATTTTCCAAC  GAGGCAAAAT      120
CTGCTTCATC  CCTCGGTACC  GGTTCCAGAG  CAATCACATG  GATATGGTGA  GAATAGAATC      180
ACCAGAGGAA  ATTTCTTTAC  TTCCCAAAAC  ATCCTGGAAT  ATCCCTCAGC  CTGGTGAGGG      240
TGATGTTCGG  GAGGAGGCCT  TGTCCACAGG  GGGACTTGAT  CTCATCTTCA  TGCCAGGCCT      300
TGGGTTTGAC  AAACATGGCA  ACCGACTGGG  GAGGGGCTAC  TATGATGCCT  ATCTGAAGCG      360
CTGTTTGCAG  CATCAGGAAG  TGAAGCCCTA  CACCTACACC  CTGGCGTTGG  CTTTCAAAGA      420
ACAGATTTGC  CTCCAGGTCC  CAGTGAATGA  AAACGACATG  AAGGTAGATG  AAGTCCTTT       479
```

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear     ( i i ) MOLECULE TYPE: peptide     ( i i i ) HYPOTHETICAL: NO     ( i v ) ANTI-SENSE: NO     ( v ) FRAGMENT TYPE: N-terminal     ( x i ) SEQUENCE DESCRIPTION: SEQ ID NO:2:

```
Phe  Asp  Lys  His  Gly  Asn  Arg  Leu  Gly  Arg  Gly  Lys
 1              5                        10
```

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO ( x i ) SEQUENCE DESCRIPTION: SEQ ID NO:3:

CCCTCGAGGT CGACGGTATC GT 22

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear     ( i i ) MOLECULE TYPE: peptide     ( i i i ) HYPOTHETICAL: NO     ( i v ) ANTI-SENSE: NO     ( v ) FRAGMENT TYPE: N-terminal     ( x i ) SEQUENCE DESCRIPTION: SEQ ID NO:4:

Pro Gly Leu Gly Phe Asp
1               5

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear     ( i i ) MOLECULE TYPE: peptide     ( i i i ) HYPOTHETICAL: NO     ( i v ) ANTI-SENSE: NO     ( v ) FRAGMENT TYPE: N-terminal     ( x i ) SEQUENCE DESCRIPTION: SEQ ID NO:5:

Gln Ile Cys Leu Gln Val Pro Val Asn Glu
1               5                   10

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear     ( i i ) MOLECULE TYPE: peptide     ( i i i ) HYPOTHETICAL: NO     ( i v ) ANTI-SENSE: NO     ( v ) FRAGMENT TYPE: N-terminal     ( x i ) SEQUENCE DESCRIPTION: SEQ ID NO:6:

Arg Ala Cys Glu
1

( 2 ) INFORMATION FOR SEQ ID NO:7:

( i ) SEQUENCE CHARACTERISTICS:
        ( A ) LENGTH: 184 amino acids
        ( B ) TYPE: amino acid
        ( C ) STRANDEDNESS: single
        ( D ) TOPOLOGY: linear     ( i i ) MOLECULE TYPE: protein

5,389,516

(iii) HYPOTHETICAL: NO (iv) ANTI-SENSE: NO (v) FRAGMENT TYPE: N-terminal (xi) SEQUENCE DESCRIPTION: SEQ ID NO:7:

```
Met Ile Arg Gln Arg Arg Arg Ala Leu Thr Pro Glu Gln Gln Glu
 1               5                  10                  15

Met Gly Gln Gln Ala Ala Thr Arg Met Met Thr Tyr Pro Pro Val Val
                20                  25                  30

Met Ala His Thr Val Ala Val Phe Leu Ser Phe Asp Gly Glu Leu Asp
            35                  40                  45

Thr Gln Pro Leu Ile Glu Gln Leu Trp Arg Ala Gly Lys Arg Val Tyr
        50                  55                  60

Leu Pro Val Leu His Pro Phe Ser Ala Gly Asn Leu Leu Phe Leu Asn
65                  70                  75                   80

Tyr His Pro Gln Ser Glu Leu Val Met Asn Arg Leu Lys Ile His
                85                  90                  95

Glu Pro Lys Leu Asp Val Arg Asp Val Leu Pro Leu Ser Arg Leu
                100                 105                 110

Asp Val Leu Ile Thr Pro Leu Val Ala Phe Asp Glu Tyr Gly Gln
                115                 120                 125

Arg Leu Gly Met Gly Gly Gly Phe Tyr Asp Arg Thr Leu Gln Asn
                130                 135                 140

Trp Gln His Tyr His Tyr Lys Thr Gln Pro Val Gly Tyr Ala His
                145                 150                 155

Asp Cys Gln Leu Val Glu Lys Leu Pro Val Glu Glu Trp Asp Ile
                160                 165                 170

Pro Leu Pro Ala Val Val Thr Pro Ser Lys Val Trp Glu Trp
                175                 180
```

(2) INFORMATION FOR SEQ ID NO:8:

(i) SEQUENCE CHARACTERISTICS:
(A) LENGTH: 164 amino acids
(B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:8:

```
Met Val Lys Pro His Leu Tyr Gln Lys Tyr Lys Arg Ile Ser Ile
 1               5                  10                  15

Phe Leu Ser Met Gln Asp Glu Ile Glu Thr Glu Glu Ile Ile Lys
                20                  25                  30

Asp Ile Phe Gln Arg Gly Lys Ile Cys Phe Ile Pro Arg Tyr Arg
                35                  40                  45

Phe Gln Ser Asn His Met Asp Met Val Arg Ile Glu Ser Pro Glu
                50                  55                  60

Glu Ile Ser Leu Leu Pro Lys Thr Ser Trp Asn Ile Pro Gln Pro
                65                  70                  75

Gly Glu Gly Asp Val Arg Glu Glu Ala Leu Ser Thr Gly Gly Leu
                80                  85                  90

Asp Leu Ile Phe Met Pro Gly Leu Gly Phe Asp Lys His Gly Asn
```

```
                       95                         100                       105
         Arg  Leu  Gly  Arg  Gly  Lys  Gly  Tyr  Tyr  Asp  Ala  Tyr  Leu  Lys  Arg
                       110                        115                       120

Cys  Leu  Gln  His  Gln  Glu  Val  Lys  Pro  Tyr  Thr  Leu  Ala  Leu  Ala
                       125                        130                       135

Phe  Lys  Glu  Gln  Ile  Cys  Leu  Gln  Val  Pro  Val  Asn  Glu  Asn  Asp
                       140                        145                       150

Met  Lys  Val  Asp  Glu  Val  Leu  Tyr  Glu  Asp  Ser  Ser  Thr  Ala
                       155                        160
```

( 2 ) INFORMATION FOR SEQ ID NO:9:

( i ) SEQUENCE CHARACTERISTICS:
        ( A ) LENGTH: 867 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( i x ) FEATURE:
        ( A ) NAME/KEY: CDS
        ( B ) LOCATION: 126..620

( x i ) SEQUENCE DESCRIPTION: SEQ ID NO:9:

```
GCGACACTTA   TAAAATAACT   TGCATCTAGG   CTGGGCGTGG   CGGCTCACGC   TGTAATCCCA         60

GCACTTTGGG   AGGCCGAAGT   GGGTGGATCA   CTTGAGGCCA   GGAGTTTGAG   ACCAGCCTGG        120

CCAAC ATG GTG AAA CCC CAT CTC TAT CAG AAA TAC AAA AGA ATT TCC                      167
      Met Val Lys Pro His Leu Tyr Gln Lys Tyr Lys Arg Ile Ser
       1               5                   10

ATC TTT CTG AGC ATG CAA GAT GAA ATT GAG ACA GAA GAG ATC ATC AAG                    215
Ile Phe Leu Ser Met Gln Asp Glu Ile Glu Thr Glu Glu Ile Ile Lys
 15              20                  25                  30

GAC ATT TTC CAA CGA GGC AAA ATC TGC TTC ATC CCT CGG TAC CGG TTC                    263
Asp Ile Phe Gln Arg Gly Lys Ile Cys Phe Ile Pro Arg Tyr Arg Phe
                 35                  40                  45

CAG AGC AAT CAC ATG GAT ATG GTG AGA ATA GAA TCA CCA GAG GAA ATT                    311
Gln Ser Asn His Met Asp Met Val Arg Ile Glu Ser Pro Glu Glu Ile
             50                  55                  60

TCT TTA CTT CCC AAA ACA TCC TGG AAT ATC CCT CAG CCT GGT GAG GGT                    359
Ser Leu Leu Pro Lys Thr Ser Trp Asn Ile Pro Gln Pro Gly Glu Gly
         65                  70                  75

GAT GTT CGG GAG GAG GCC TTG TCC ACA GGG GGA CTT GAT CTC ATC TTC                    407
Asp Val Arg Glu Glu Ala Leu Ser Thr Gly Gly Leu Asp Leu Ile Phe
     80                  85                  90

ATG CCA GGC CTT GGG TTT GAC AAA CAT GGC AAC CGA CTG GGG AGG GGC                    455
Met Pro Gly Leu Gly Phe Asp Lys His Gly Asn Arg Leu Gly Arg Gly
 95                  100                 105                 110

AAG GGC TAC TAT GAT GCC TAT CTG AAG CGC TGT TTG CAG CAT CAG GAA                    503
Lys Gly Tyr Tyr Asp Ala Tyr Leu Lys Arg Cys Leu Gln His Gln Glu
                 115                 120                 125

GTG AAG CCC TAC ACC CTG GCG TTG GCT TTC AAA GAA CAG ATT TGC CTC                    551
Val Lys Pro Tyr Thr Leu Ala Leu Ala Phe Lys Glu Gln Ile Cys Leu
             130                 135                 140

CAG GTC CCA GTG AAT GAA AAC GAC ATG AAG GTA GAT GAA GTC CTT TAC                    599
Gln Val Pro Val Asn Glu Asn Asp Met Lys Val Asp Glu Val Leu Tyr
         145                 150                 155

GAA GAC TCG TCA ACA GCT TAA ATCTGGATTA CTACAGCCAA ATAATCAGTG                       650
Glu Asp Ser Ser Thr Ala *
     160                 165
```

```
TTTTATATGA GAGTAAAGCA AAGTATGTGT ATTTTTCCCT TGTCAAAAAT TAGTTGAAAT    710

TGTTCATTAA TGTGAATACA GACTGCATTT TAAAATTGTA ATTATGAAAT ACCTTATATA    770

AAACCATCTT TAAAAACCAA TAGAAGTGTG AATAGTAGAA TATTAATTAA AATGGAGGCT    830

ATCAGCCTGT GATTTCAGC TTAAAAAAAA AAAAAA                               867
```